United States Patent [19]
Bartlett et al.

[11] Patent Number: 4,543,202
[45] Date of Patent: Sep. 24, 1985

[54] AEROSOL PROPELLANT COMPOSITIONS

[75] Inventors: Philip L. Bartlett; John J. Daly, Jr.; John D. Sterling, Jr., all of Wilmington, Del.

[73] Assignee: E. I. Du Pont de Nemours and Company, Wilmington, Del.

[21] Appl. No.: 592,881

[22] Filed: Mar. 23, 1984

[51] Int. Cl.[4] .................................. C09K 3/30
[52] U.S. Cl. ......................... 252/305; 252/90; 252/522 R; 424/45; 424/47; 424/DIG. 1; 426/609; 426/811
[58] Field of Search .................. 252/305, DIG. 9; 424/45, 47, DIG. 1

[56] References Cited
U.S. PATENT DOCUMENTS 3,207,386  9/1965  Presant et al. ............... 424/47 X
4,174,295  11/1979  Bargigia et al. ............. 424/45 X

OTHER PUBLICATIONS

Du Pont DYMEL Aerosol Propellant Systems Data Sheet, 2nd Quarter, 1983.
J. D. Sterling, "Fluorocarbon and Dimethyl Ether Aerosol Propellants", published in Aerosol Age, vol. 27, No. 12, Dec. 1982, pp. 48, 50 and 52.

Primary Examiner—Richard D. Lovering

[57] ABSTRACT

Propellant gas compositions for aerosol products consisting essentially of monochlorodifluoromethane, dimethyl ether and 1-chloro-1,1-difluoroethane, said compositions having a vapor pressure of about 50 to 60 psig at 70° F.

2 Claims, 1 Drawing Figure

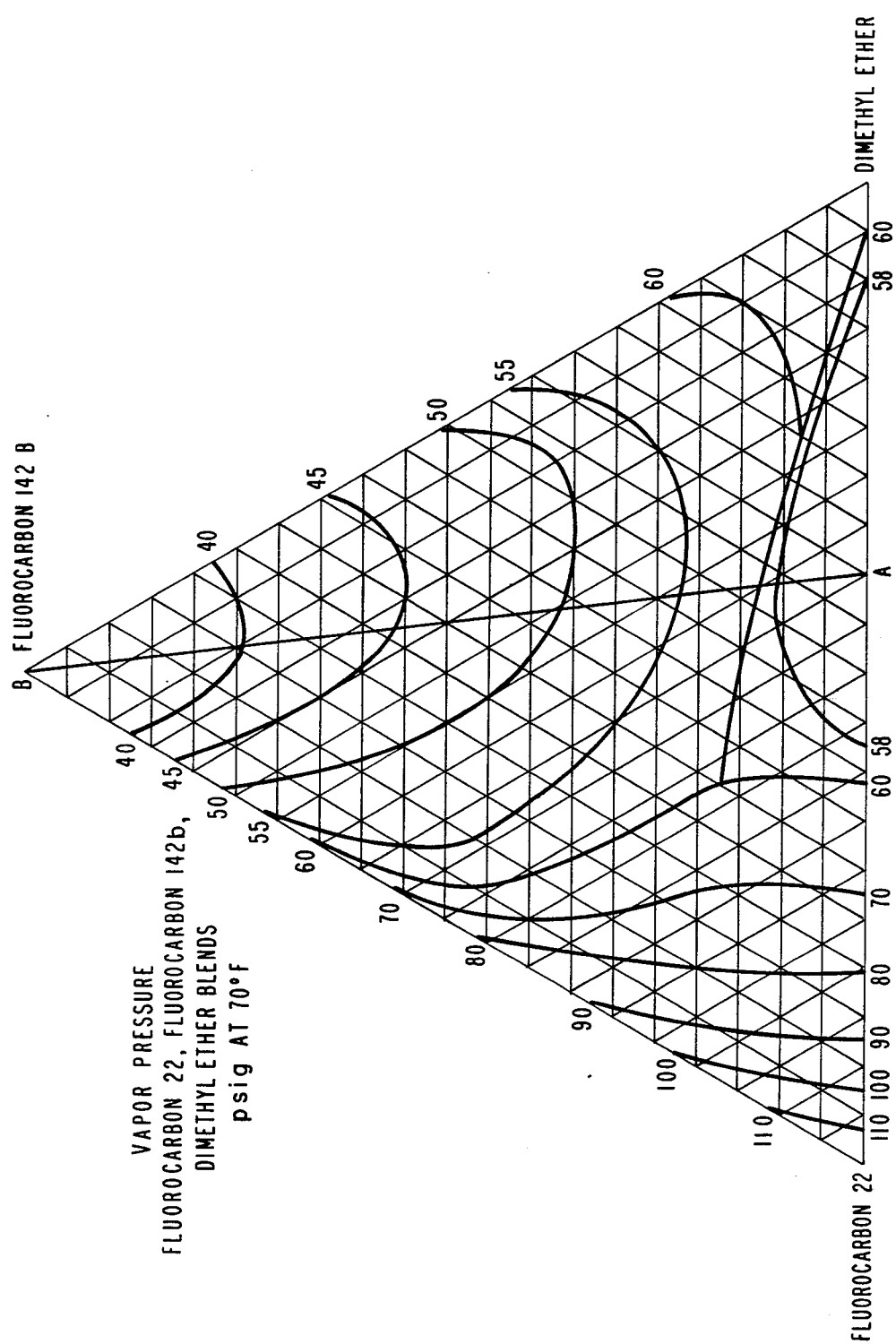

AEROSOL PROPELLANT COMPOSITIONS

BACKGROUND OF THE INVENTION

1. Field of the Invention

This invention relates to propelling gas systems for aerosol products.

2. Description of the Prior Art

Many products designed for household, personal or industrial use are available as aerosol products. Typical examples of such products and ones in which the propellant system of the present invention can be used include household products such as waxes, polishes, pan sprays, room fresheners and household insecticides; industrial products such as cleaners, lubricants, and mold release agents; and automotive products such as cleaners and polishes. All such products utilize the pressure of a propellant gas or a mixture of propellant gases (i.e., a propellant gas system) to expel the active ingredients from the container. For this purpose, most aerosols employ liquified gases which vaporize and provide the pressure to propel the active ingredients when the valve on the aerosol container is pressed open.

An important physical property associated with the dispensing of aerosol products is the vapor pressure of the propellant. Vapor pressure from the viewpoint of this invention is the pressure exerted when a liquified propellant gas is in equilibrium with its vapor in a closed container, such as an aerosol can. Vapor pressure can be measured by connecting a pressure gauge to the valve on an aerosol can or gas cylinder containing the vapor/liquid mixture. A standard of measurement of vapor pressure in the U.S. aerosol industry is pounds per square inch gauge (psig) with the gas/liquid mixture at constant temperature, most commonly at 70° F. When vapor pressure is mentioned in the ensuing specification without reference to temperature, it can be assumed that the pressure is determined at 70° F. The vapor pressures of liquified gases most widely employed as aerosol propellants will vary over the range of about 20 to 90 psig at 70° F. However, for a great many aerosol products, propellants with a vapor pressure in the range of about 50 to 60 psig are most desirable. The propellant systems of the present invention have vapor pressures in this latter range.

SUMMARY OF THE INVENTION

The present invention pertains to aerosol propellant compositions containing the azeotrope of monochlorodifluoromethane and dimethyl ether (DME). This azeotrope which consists of 40% by weight of monochlorodifluoromethane (more commonly referred to in the industry as fluorocarbon 22 or FC-22) and 60% by weight of dimethyl ether is a maximum boiling ($-9°$ F.) minimum vapor pressure (55 psig at 70° F.) azeotrope. It has been found that this azeotrope in admixture with FC-142b (1-chloro-1,1-difluoroethane —vp 29 psig at 70° F.) produces useful aerosol propellants with a vapor pressure in the range of about 50 to 60 psig over a relatively wide range of proportions with respect to the amount of FC-142b present. FC-142b can be used with the azeotrope in amounts of about 1-37% by weight, based on the total propellant composition, and the vapor pressure of the propellant gas mixture is still within the desired range of about 50 to 60 psig. A preferred range for FC-142b content is 20-30% by weight of the total propellant gas composition.

Referring to the drawing, the diagram shown is a triangular coordinate chart of the type commonly used in the aerosol industry to illustrate the relationship of concentration and vapor pressure for 3-component systems. In the chart as shown, a concentration of 100% by weight of a particular component is at the vertex of the triangle where the name of the component appears. A concentration of zero percent of this same component is on the side of the triangle opposite this vertex. A composition representing $33\frac{1}{3}\%$ by weight of each component is at the center of the triangle. The parallel lines leading away from each vertex are spaced at 5 weight percent intervals. The curved lines within the triangle with the same number appearing at each end of the line indicate the makeup of formulations of the three components that exert a vapor pressure designated by the number at the end of the line. These lines are the result of measuring the vapor pressure of a large number of specific compositions until sufficient data points are obtained to accurately draw each vapor pressure line. Each of these vapor pressure lines represents one particular pressure. There is also shown on the chart a line AB extending from the base of the triangle at the point (40/60) representing the composition of the FC-22/DME azeotrope to the apex of the triangle at point B which represents 100% FC-142b. Determination of the vapor pressure of any given composition comprising the azeotrope and FC-142b can be quickly ascertained by locating the point on this line in the chart that corresponds to the FC-142b content of the mixture. The vapor pressure line in closest proximity to this point enables one to closely estimate the vapor pressure of the given composition. Further, it will be apparent from looking at the vapor pressure lines that cross line AB, that about 1 to 37% FC-142b can be mixed with the azeotrope to produce compositions with vapor pressures that stay within the range of about 50 to 60 psig.

While the preferred mixtures of FC-22 dimethyl ether and FC-142b are those in which the ratio of FC-22 to dimethyl ether corresponds to the azeotrope of these two components (i.e., a 40:60 ratio of FC-22 to DME), it can be seen from the triangular coordinate chart that vapor pressures within the range of about 50 to 60 psig can also be obtained in three-component mixtures where the ratio of FC-22 to DME falls on either side of the azeotrope. For example, 1–37% FC-142b can be added to a 50/50 mixture of FC-22 and DME and to a 30/70 mixture of FC-22 and DME without substantially modifying the vapor pressure of the propellant. Thus, the broad embodiment of this invention comprises three-component compositions of FC-22, dimethylether and FC-142b in which the vapor pressure is in the range of about 50 to 60 psig. This would include compositions in which the ratio of FC-22 and DME components are in the ratio of 40:60 and those in which the FC-22/DME is outside this ratio but within the specified vapor pressure range. The proportion of components in such composition can be ascertained from the diagram in the drawing.

The tendency for little variation in vapor pressure over a wide range of compositions is considered to be unexpected. The present invention involves, in essence, the incorporation of an additional component (FC-142b) with the FC-22/dimethyl ether azeotrope. Since an azeotrope behaves in liquid/vapor equilibrium as if it were a single compound, it might be expected that with the addition of appreciable quantities of a third component, the vapor pressure of the admixture would be somewhere in the middle area between that of the azeotrope and the third component. Thus, the addition of, for example, 35% of FC-142b (vp 29 psig) to the FC-22/DME azeotrope (vp 55 psig) would be expected to significantly reduce the vp of the ternary blend. However, within the defined limits of the present invention there is essentially little change from the vapor pressure of the azeotrope itself.

The vapor pressure of the FC-22/DME azeotrope is in a desirable range for aerosol propellants, and there is substantially little change in such pressures as the amount of FC-142b is varied within the limits set forth herein.

Further, the presence of FC-22, FC-142b and DME contributes lower flammability characteristics to aerosol formulations as compared to the use of a hydrocarbon propellant blend of similar vapor pressure; i.e., FC-22 is nonflammable and DME and FC-142b are less flammable than typical hydrocarbon propellants such as propane, butane, and isobutane. Although the gas mixtures of the present invention are themselves flammable and explosion-proof equipment should be used in the loading of aerosol cans, the presence of FC-22 and FC-142b in the mixture will reduce the flammability of many aerosol products to such a degree that special labeling is not required under the Federal Hazardous Substances Act.

In addition to its low flammability, FC-142b possesses an additional important characteristic. FC-142b is known to enhance the fragrance of aerosol colognes. Thus, a propellant mixture containing as little as 10 wt. % FC-142b will produce a more powerful odor sensation than that experienced without FC-142b. This fragrance enhancement allows a formulator to use less amounts of expensive fragrance oils in his formulation without sacrificing quality of product.

In summary, mixtures of FC-22, DME and FC-142b can be varied in composition over a wide range to produce changes in such important properties as flammability and fragrance enhancement without essentially changing vapor pressure of the propellant blend.

EXAMPLES

The following examples are typical of the aerosol propellant systems of the present invention and their use in aerosol products. These examples are presented for the purpose of illustrating the vapor pressure and flammability properties of the propellants of the present invention, and specific formulations in these examples may require toxicity testing and governmental approval prior to actual use.

Procedure

Examples 1–5 were prepared according to the following procedure. The active ingredients were weighed into a six-ounce three-piece aerosol can 2⅛" in diameter and 4⅜" long. The can was purged with dichlorodifluoromethane (FC-12) vapor to displace the air in the container. The aerosol can valve was then placed into the can and crimped. The propellants were introduced into the can as liquids through the aerosol valve. Volume amounts corresponding to the weights of the propellants were calculated prior to loading, and a glass, calibrated, pressure buret was used to measure and transfer the liquids from storage cylinders to the can. A nitrogen gas pressure of 100 psig was applied to the buret to aid in transferring the liquids from the buret to the can. After the propellant was loaded, the can was weighed, and the weight of propellant recorded. The loaded can was placed in a 70° F. water bath for 30 minutes and the pressure was then measured with a pressure gauge. Also included in the examples is the vapor pressure for the propellant mixtures without active ingredients. The values were obtained from the triangular chart in the drawing. The flame extension and flashback tests were conducted by spraying the samples across a candle flame from a distance of six inches and recording how far the flame extended beyond the candle and how far it flashed back towards the can. The preparation and testing of the sample of Examples 6 and 7 also used the procedures described above, except that the aerosol ingredients were loaded into clear, plastic-coated, four-ounce, glass aerosol bottles instead of aerosol cans.

EXAMPLE 1

An illustration of a system useful as a pan spray (antistick) is as follows:

| Formulation | Wt. % of Propellant | Wt. % of Total Ingredients | Grams/Can |
| --- | --- | --- | --- |
| Active Ingredients | | | |
| Lecithin | — | 25.0 | 25.0 |
| Soybean Oil | — | 25.0 | 25.0 |
| Propellant | | | |
| FC-22 | 28.0 | 14.0 | 14.1 |
| DME | 42.0 | 21.0 | 21.2 |
| FC-142b | 30.0 | 15.0 | 15.2 |
| Vapor Pressure of Propellant (psig at 70° F.) | | 52 | |
| Vapor Pressure of Filled Can (psig at 70° F.) | | 51 | |
| Flame Extension (inches) | | 12 | |
| Flashback (inches) | | 4 | |
| Value | | Seaquist NS-34 | |
| Body | | Capillary | |
| Stem (inches) | | .013 | |
| Actuator (inches) | | .010 | |

EXAMPLE 2

An illustration of a system useful as a pan spray is as follows:

| Formulation | Wt. % of Propellant | Wt. % of Total Ingredients | Grams/Can |
| --- | --- | --- | --- |
| Active Ingredient | | | |
| Silicone (350 cs. food grade) | — | 25.0 | 25.0 |
| Propellant | | | |
| FC-22 | 28.0 | 21.0 | 21.1 |
| DME | 42.0 | 31.5 | 31.7 |
| FC-142b | 30.0 | 22.5 | 22.6 |
| Vapor Pressure of Propellant (psig at 70° F.) | | 52 | |
| Vapor Pressure of Filled Can (psig at 70° F.) | | 51 | |
| Flame Extension (inches) | | 6 | |
| Flashback (inches) | | 0 | |
| Valve | | Seaquist NS-34 | |
| Body | | Capillary | |
| Stem (inches) | | .013 | |
| Actuator (inches) | | .010 | |

EXAMPLE 3

An illustration of a system useful as a hair spray is as follows:

| Formulation | Wt. % of Propellant | Wt. % of Total Ingredients | Grams/Can |
|---|---|---|---|
| Active Ingredients | | | |
| Vinyl Pyrrolidone Vinyl Acetate Copolymer | — | 4.00 | 4.0 |
| Coconut Monoethanol-Amide Surfactant | — | 0.10 | 0.1 |
| Silicone | — | 0.05 | 0.05 |
| Ethyl Alcohol | — | 40.85 | 40.85 |
| Propellant | | | |
| FC-22 | 30.9 | 17.00 | 17.2 |
| DME | 46.5 | 25.60 | 25.7 |
| FC-142b | 22.6 | 12.40 | 12.9 |
| Vapor Pressure of Propellant (psig at 70° F.) | | 55 | |
| Vapor Pressure of Filled Can (psig at 70° F.) | | 38 | |
| Flame Extension (inches) | | 16 | |
| Flashback (inches) | | 5 | |
| Valve | | Seaquist ST-71 | |
| Body (inches) | | .013 | |
| Stem (inches) | | .013 | |
| Actuator (inches) | | .013 | |

EXAMPLE 4

An illustration of a system useful as a hair spray is as follows:

| Formulation | Wt. % of Propellant | Wt. % of Total Ingredients | Grams/Can |
|---|---|---|---|
| Active Ingredients | | | |
| Amphoteric Acrylic Resin | — | 1.80 | 1.8 |
| 2-amino-2-methyl-1-propanol | — | 0.30 | 0.3 |
| Coconut Monoethanol-amide Surfactant | — | 0.10 | 0.1 |
| Silicone | — | 0.05 | 0.05 |
| Ethyl Alcohol | — | 42.75 | 42.75 |
| Propellant | | | |
| FC-22 | 28.0 | 15.40 | 15.2 |
| DME | 42.0 | 23.10 | 22.8 |
| FC-142b | 30.0 | 16.50 | 16.7 |
| Vapor Pressure of Propellant (psig at 70° F.) | | 52 | |
| Vapor Pressure of Filled Can (psig at 70° F.) | | 38 | |
| Flame Extension (inches) | | 16 | |
| Flashback (inches) | | 5 | |
| Valve | | Seaquist ST-71 | |
| Body | | .013 | |
| Stem | | .013 | |
| Actuator | | .013 | |

EXAMPLE 5

An illustration of a system useful as a hair spray is as follows:

| Formulation | Wt. % of Propellant | Wt. % of Total Ingredients | Grams/Can |
|---|---|---|---|
| Active Ingredients | | | |
| Carboxylated Vinyl Acetate Terpolymer | — | 2.50 | 2.5 |
| 2-amino-2-methyl-1-propanol | — | 0.20 | 0.2 |
| Coconut Monoethanol-amide Surfactant | — | 0.10 | 0.1 |
| Silicone | — | 0.05 | 0.05 |
| Ethyl Alcohol | — | 47.15 | 47.15 |
| Propellant | | | |
| FC-22 | 28.0 | 14.00 | 13.8 |
| DME | 42.0 | 21.00 | 20.8 |
| FC-142b | 30.0 | 15.00 | 15.4 |
| Vapor Pressure of Propellant (psig at 70° F.) | | 52 | |
| Vapor Pressure of Filled Can (psig at 70° F.) | | 36 | |
| Flame Extension (inches) | | 16 | |
| Flashback (inches) | | 5 | |
| Valve | | Seaquist ST-71 | |
| Body (inches) | | .013 | |
| Stem (inches) | | .013 | |
| Actuator (inches) | | .013 | |

EXAMPLE 6

An illustration of a system useful as a cologne is as follows:

| Formulation | Wt. % of Propellant | Wt. % of Total Ingredients | Grams/Can |
|---|---|---|---|
| Active Ingredients | | | |
| Fragrance Oil | — | 4.0 | 4.0 |
| Ethyl Alcohol | — | 65.0 | 65.0 |
| Propellant | | | |
| FC-22 | 36.1 | 11.2 | 11.3 |
| DME | 53.9 | 16.7 | 16.7 |
| FC-142b | 10.0 | 3.1 | 3.2 |
| Vapor Pressure of Propellant (psig at 70° F.) | | 58 | |
| Vapor Pressure of Filled Bottle (psig at 70° F.) | | 22 | |
| Flame Extension (inches) | | 8 | |
| Flashback (inches) | | 5 | |
| Valve | | Emson bottle valve S20T | |
| Stem (inches) | | .013 | |
| Gasket | | S-8501 | |
| Actuator | | A-7MB Conical | |

EXAMPLE 7

An illustration of a system useful as a cologne is as follows:

| Formulation | Wt. % of Propellant | Wt. % of Total Ingredients | Grams/Can |
|---|---|---|---|
| Active Ingredients | | | |
| Fragrance Oil | — | 4.0 | 4.0 |
| Ethyl Alcohol | — | 65.0 | 65.0 |
| Propellant | | | |
| FC-22 | 28.1 | 8.7 | 8.6 |
| DME | 41.0 | 13.0 | 12.9 |
| FC-142b | 30.0 | 9.3 | 9.4 |
| Vapor Pressure of Propellant (psig at 70° F.) | | 53 | |
| Vapor Pressure of Filled Bottle (psig at 70° F.) | | 20 | |
| Flame Extension (inches) | | 8 | |
| Flashback (inches) | | 5 | |
| Valve | | Emson bottle valve S20T | |
| Stem (inches) | | .013 | |
| Gasket | | S-8501 | |
| Actuator | | A-7MB Conical | |

We claim:

1. An aerosol composition comprising 1–37% by weight of 1-chloro-1,1-difluoroethane, the balance being a mixture of monochlorodifluoromethane and dimethyl ether in a 40/60 weight ratio.

2. The composition of claim 1 in which the 1-chloro-1,1-difluoroethane is present in an amount of about 20–30% by weight.

* * * * *